(12) United States Patent
Blain et al.

(10) Patent No.: US 8,500,811 B2
(45) Date of Patent: Aug. 6, 2013

(54) DEVICE AND METHOD FOR DELIVERY OF MULTIPLE HETEROGENOUS ORTHOPEDIC IMPLANTS

(75) Inventors: Jason Blain, Encinitas, CA (US); Greg Martin, Encinitas, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 786 days.

(21) Appl. No.: 12/167,173

(22) Filed: Jul. 2, 2008

(65) Prior Publication Data

US 2009/0012529 A1    Jan. 8, 2009

Related U.S. Application Data

(60) Provisional application No. 60/947,596, filed on Jul. 2, 2007.

(51) Int. Cl.
*A61F 2/44* (2006.01)

(52) U.S. Cl.
USPC .......................................... 623/17.11; 606/99

(58) Field of Classification Search
USPC .............. 623/17.11–17.16; 606/90, 246–253, 606/279, 86 A, 99–100
See application file for complete search history.

(56) References Cited

U.S. PATENT DOCUMENTS

| | | | | |
|---|---|---|---|---|
| 5,489,307 A | * | 2/1996 | Kuslich et al. | 128/898 |
| 5,885,299 A | * | 3/1999 | Winslow et al. | 606/99 |
| 6,056,749 A | * | 5/2000 | Kuslich | 606/86 A |
| D524,443 S | | 7/2006 | Blain | |
| D533,277 S | | 12/2006 | Blain | |
| D539,934 S | | 4/2007 | Blain | |
| D541,940 S | | 5/2007 | Blain | |
| 2002/0022845 A1 | * | 2/2002 | Zdeblick et al. | 606/80 |
| 2006/0201289 A1 | * | 9/2006 | Davidson et al. | 81/177.85 |
| 2008/0161925 A1 | * | 7/2008 | Brittan et al. | 623/17.16 |

* cited by examiner

*Primary Examiner* — Nicholas Woodall
*Assistant Examiner* — Melissa A Hall
(74) *Attorney, Agent, or Firm* — Knobbe, Martens, Olson & Bear, LLP

(57) ABSTRACT

An orthopedic coupling device is used for simultaneous attachment of multiple heterogeneous orthopedic components, such as a spacer and plate, for implantation in the body. The device coupler includes a coupling base, at least one coupling member configured to attach to one an orthopedic spacer while also trapping or clamping an orthopedic fixation plate between the coupling base and the orthopedic spacer. The orthopedic coupler device may have a detachable handle to facilitate access and visibility of the spacer and plate after initial implantation.

24 Claims, 6 Drawing Sheets

FIG. 3A
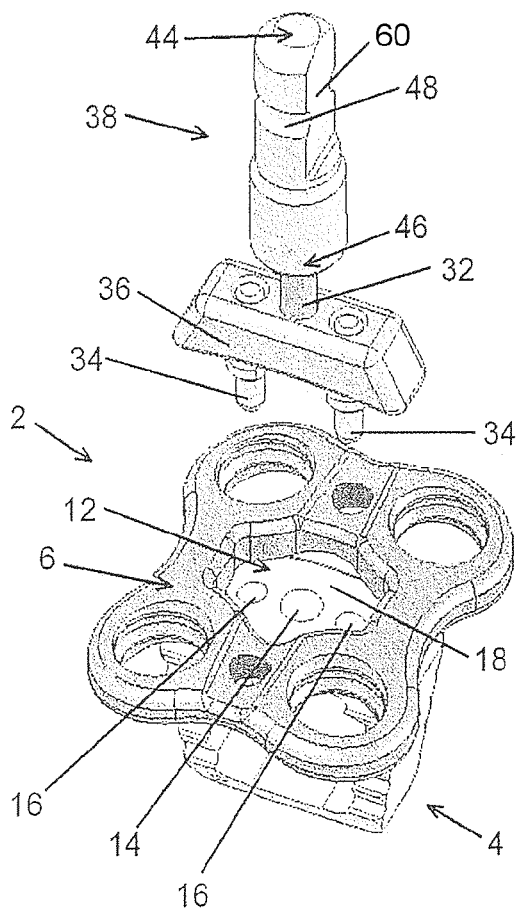
FIG. 3B
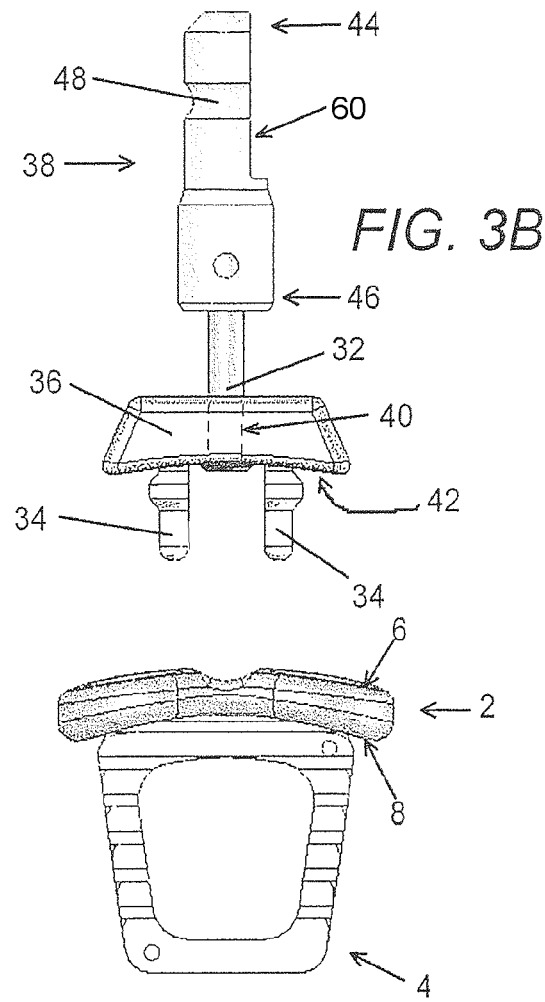
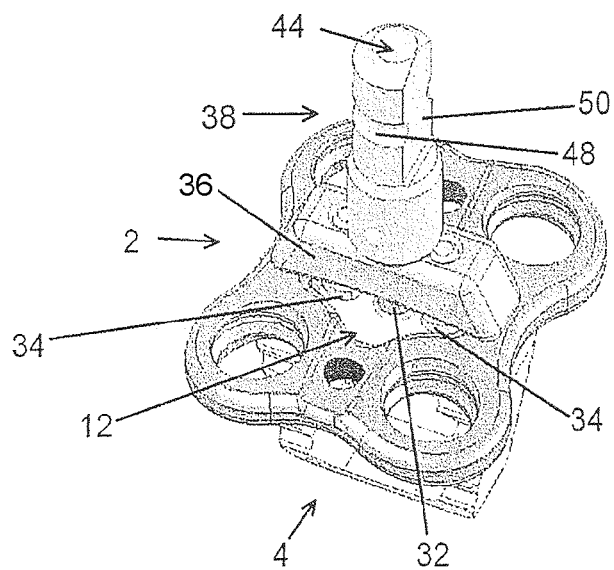
FIG. 3C

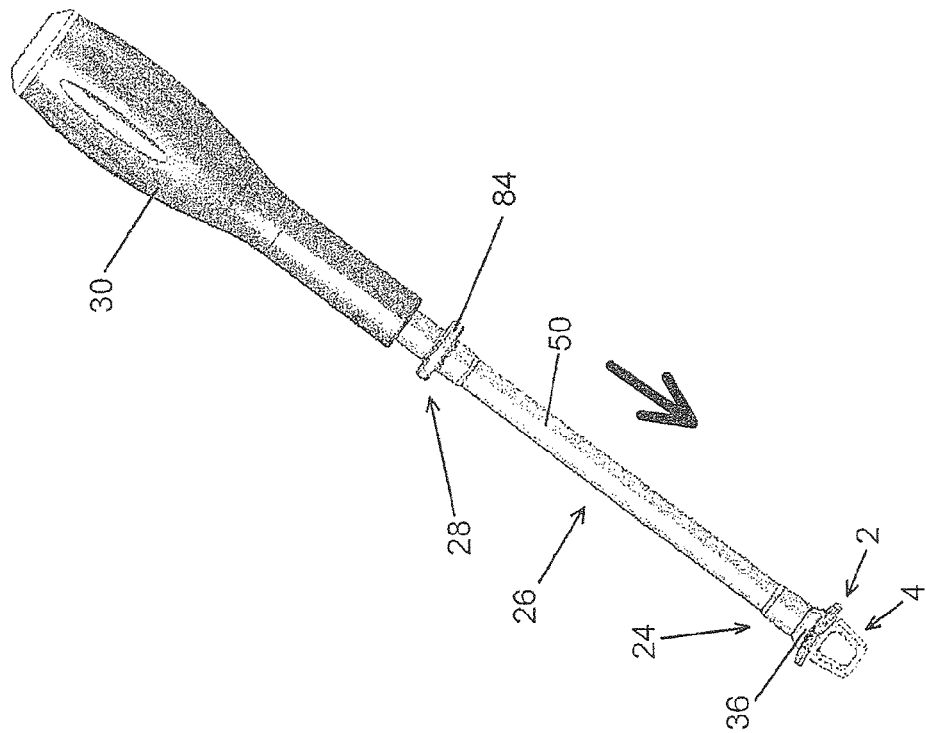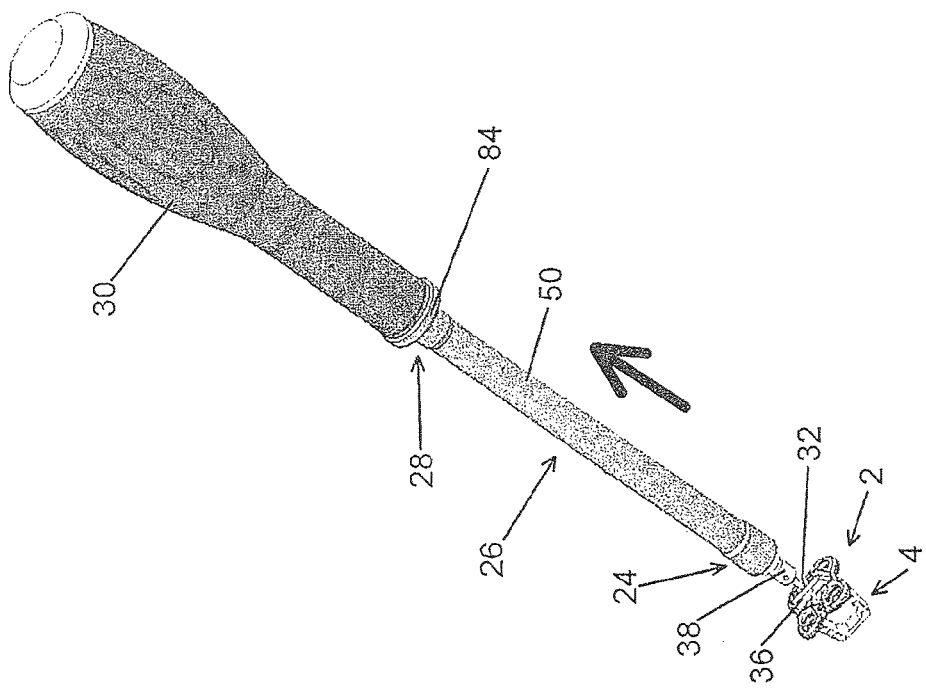

DEVICE AND METHOD FOR DELIVERY OF MULTIPLE HETEROGENOUS ORTHOPEDIC IMPLANTS

CROSS-REFERENCE TO RELATED APPLICATIONS

The present application claims priority under 35 U.S.C. §119(e) to U.S. Provisional Application No. 60/947,596 filed on Jul. 2, 2007, the disclosure of which is hereby incorporated by reference herein in its entirety.

BACKGROUND OF THE INVENTION

1. Field of the Invention

The invention relates generally to systems and methods for performing spinal fixation. Specifically, the invention relates to coupler devices for simultaneous coupling and delivery of multiple, separate vertebral plates and interbody fusion devices together during implantation, particularly those used for spinal orthopedic procedures.

2. Description of the Related Art

Advancing age, as well as injury, can lead to degenerative changes in the bones, discs, joints, and ligaments of the spine, producing pain and instability. Under certain circumstances, alleviation of the problems can be provided by performing spinal fusion. Spinal fusion is a surgical technique in which two or more vertebrae of the spinal column are fused together to eliminate the motion between the fused vertebrae. Spinal fusion is used to treat conditions where the spine exhibits instability. Spine instability may result from causes such as fracture, scoliosis, and spondylolisthesis, where one or more vertebrae move in a forward direction relative to the other vertebrae. Spinal fusion with discectomy is also performed for herniations of the discs. This surgery involves removal of the affected disc and fusion of the adjacent vertebrae. Traditionally, bone grafts have been used to fuse the vertebrae, but various types of vertebral implants have also been used.

The use of bone fixation systems for treating bone conditions is well established. For example, a bone plate may be positioned over and surrounding the bone injury area and secured to the bone. The bone plate can be secured to the bone by bone screws or other similar fasteners inserted through holes in the bone plate and into the bone itself. The screws are tightened so that the bone plate holds the bone to be treated in place in order to insure proper healing. Early fixation devices tended to be applicable only to long-bone injuries, with only limited uses for lower lumbar spinal injuries and disorders. The use of plate/screw fixation systems later expanded, however, to include uses for spinal injuries, including fusion of vertebrae and fixation devices for treating cervical vertebrae injuries.

SUMMARY OF THE INVENTION

The invention relates generally to delivery devices that may be used to deliver multiple medical components to an implantation site. Such a delivery device may be useful where access to the surgical site is difficult to achieve and the implantation procedure is simplified if the delivery tool does not need to be repeatedly removed from the surgical site. Such a delivery device may also be useful to maintain a particular spatial relationship or alignment between the multiple components. This may be beneficial in situations where malpositioning of one component may interfere with the positioning or function of another component.

In one embodiment, an orthopedic coupler device for the simultaneous delivery of multiple heterogeneous orthopedic components, such as a spacer and plate, is provided. The device coupler includes a coupling base, at least one coupling member configured to attach to one an orthopedic spacer while also trapping or clamping an orthopedic fixation plate between the coupling base and the orthopedic spacer. The orthopedic coupler device may have a detachable handle to facilitate access and visibility of the spacer and plate after initial implantation.

In one embodiment, a surgical delivery tool is provided, comprising an outer tubular shaft having a proximal end, a distal end and a lumen therebetween; an inner shaft having a proximal end, a distal end, wherein the inner shaft is located at least partially in the lumen of the outer tubular shaft; a handle located at the proximal end of the inner shaft; a device coupler wherein the device coupler comprises a coupling base with a through lumen and an elongate coupling member comprising a proximal end and a distal end, wherein the distal end is configured with a least one radial projecting structure, wherein at least a portion of the elongate coupling member is configured so as to move in the through lumen of the coupling base; and a releasable lock assembly located about the distal end of the outer tubular shaft and configured to releasably engage the proximal end of the elongate coupling member of the device coupler. The delivery tool may further comprise two distal coupling members fixed to the coupling base. The distal end of the inner shaft may comprise a distal lumen, a lumenal surface, an ablumenal surface, and a lock lumen between the lumenal surface and the ablumenal surface. The distal lumen of the inner shaft may comprise a non-circular cross-sectional shape. The proximal end of the elongate coupling member may have a configuration that forms a mechanical interfit with the distal lumen of the inner shaft. The lock lumen may have a lumenal opening and an ablumenal opening. The lumenal opening has at least one dimension that is smaller than the ablumenal opening. The releasable lock assembly may be located at least partially within the lock lumen of the inner shaft. The releasable lock assembly may comprise a lock element having a lock position wherein the lock element protrudes through the lumenal opening and a release position wherein the lock element does not protrude through the lumenal opening. The lumen of the outer tubular shaft may have an enlarged cross-sectional area about the distal end of the outer tubular shaft. The lock element may be a ball bearing. The delivery tool may further comprise a bias member within the lumen of the outer shaft. The bias member may be configured to bias the lock element in the lock position. The coupling base may comprise a distal concave surface. The inner shaft and the outer tubular shaft may be configured to permit at least some relative rotational movement between the inner shaft and the outer tubular shaft. The inner shaft and the outer tubular shaft may be configured to permit at least some relative axial movement between the inner shaft and the outer tubular shaft. The elongate coupling member may be integrally formed.

In another embodiment, a system for performing an orthopedic procedure is provided, comprising: a first orthopedic implant configured with a first access opening; a second orthopedic implant having a second access opening and at least one transverse dimension that is larger than the smallest transverse dimension of the first access opening; wherein the second orthopedic implant has a different configuration from the first orthopedic implant; and a delivery tool comprising a retaining surface and a distal elongate coupling member; wherein the retaining surface comprises at least one transverse dimension that is larger than the smallest transverse dimension of the first access opening; and wherein the distal elongate coupling member is configured to simultaneously pass through the first access opening of the first orthopedic implant and to form a mechanical interfit with the second access opening of the second orthopedic implant so as to retain the first orthopedic implant between the retaining surface and the second orthopedic implant. The first orthopedic implant may be a fixation plate. The second orthopedic implant may be an interbody vertebral spacer. The interbody vertebral spacer may be an interbody cervical spacer. The mechanical interfit between the delivery tool and the second access opening of the second orthopedic implant may comprise a mechanical interfit.

In another embodiment, a method for treating a patient is provided, comprising: providing an implant delivery system comprising a clamp structure, a detachably engaged distal orthopedic implant, and a proximal orthopedic implant between the clamp structure and the releasably engaged distal orthopedic implant, wherein the distal orthopedic implant has a different configuration than the proximal orthopedic implant; implanting the distal orthopedic implant to an first implantation site; implanting the proximal orthopedic implant to a second implantation site; and detaching the delivery tool from the distal orthopedic implant. The implantation site may be an intervertebral space. The second implantation site may comprise two bony surfaces of two adjacent vertebrae. The method may further comprise loosening the delivery tool to permit increased movement of the proximal orthopedic implant relative to the delivery tool. The method may further comprise retightening the delivery tool to resecure the proximal orthopedic implant relative to the delivery tool. Detaching the delivery tool from the distal orthopedic implant may occur before implanting the proximal orthopedic implant to the second implantation site. The method may further comprise fixing the distal orthopedic implant to the first implantation site. The distal orthopedic implant may be an intervertebral spacer. The proximal orthopedic implant may be vertebral fixation plate. The method may further comprise fixing the proximal orthopedic implant to the second implantation site. Implanting the distal orthopedic implant may occur before implanting the proximal orthopedic implant.

All of these embodiments are intended to be within the scope of the invention herein disclosed. These and other embodiments will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

These and other features, aspects, and advantages of the invention disclosed herein are described below with reference to the drawings of preferred embodiments, which are intended to illustrate and not to limit the invention.

FIG. 3A is a perspective view of the device coupler positioned above the separable orthopedic devices of FIGS. 1A and 1B. FIG. 3B is a top view of the device coupler of FIG. 3A in the retracted position. FIG. 3C is a perspective view of the device coupler of FIG. 3A in the extended position.

FIGS. 5A and 5B depict the coupler of FIGS. 2A and 2B coupled to two separable orthopedic devices—a bone plate and an interbody fusion implant.

DETAILED DESCRIPTION OF THE PREFERRED EMBODIMENT

Although certain preferred embodiments and examples are disclosed below, it will be understood by those in the art that the invention extends beyond the specifically disclosed embodiments and/or uses of the invention and obvious modifications and equivalents thereof. Thus, it is intended that the scope of the invention herein disclosed should not be limited by the particular disclosed embodiments described below.

Fixation procedures sometimes require the insertion of multiple orthopedic devices into the target location. Multi-step processes are generally acceptable for procedures in locations with ample space for maneuverability. However, for more restrictive regions with limited space or in close proximity to vital organs or other tissues, multi-step processes can tax the abilities of even the most dexterous of users. For example, the area surrounding the cervical vertebrae is in close proximity to the neck region, which restricts the use of instruments that can be safely manipulated near vertebral bodies. Moreover, when accessing the cervical vertebrae, for example, the proximity to the throat region further impedes the ability of the user to accurately perform a multi-step process. At least one embodiment of the present invention reflects the realization that reducing both the number of devices and tools present per step and the number of steps per procedure can reduce the risk of injury to the patient.

Figure 1A:
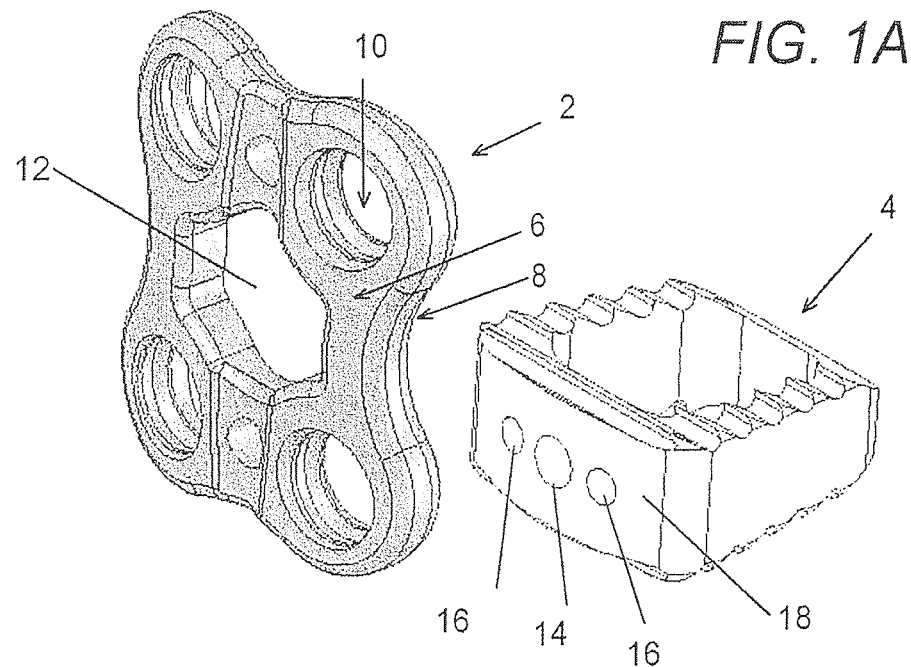
FIGS. 1A and 1B depict two separate orthopedic devices.
Figure 1B:
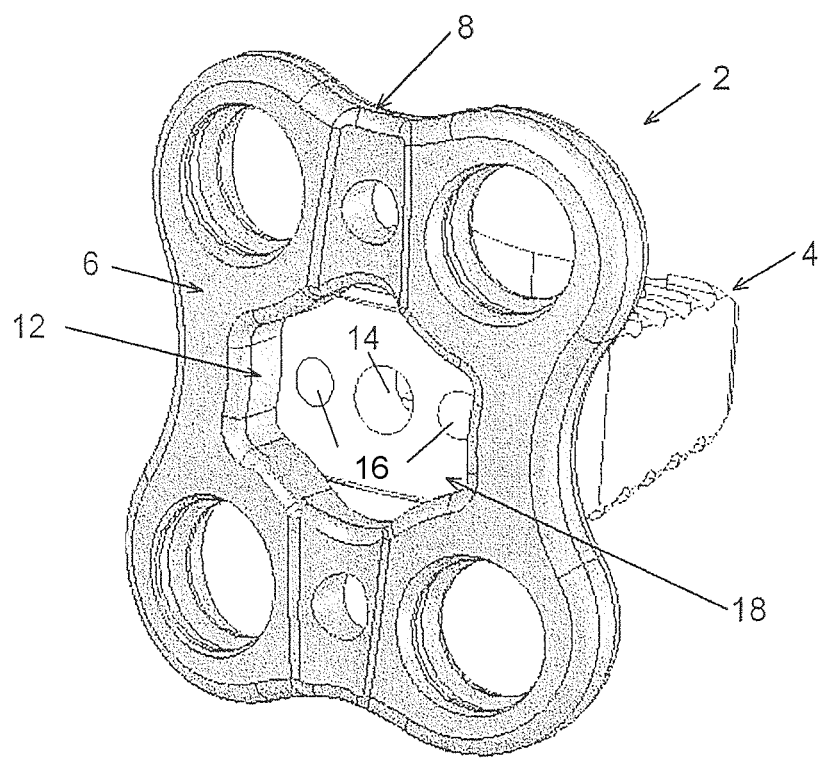

FIGS. 1A and 1B depict examples of multiple orthopedic components which can be inserted and positioned together during an orthopedic procedure. FIG. 1A depicts two separate and heterogeneous orthopedic components—a bone plate 2 and an interbody fusion spacer 4. As shown in FIG. 1A, the bone plate 2 comprises a trailing surface 6, a leading surface 8, and one or more apertures 10 for attaching the plate 2 to the vertebrae using bone screws or other fasteners. The terms "leading" and "trailing" are used for convenience to describe different surfaces on the plate 2, but should not be interpreted as limiting the plate to a particular orientation or implantation site. The bone plate 2 may optionally comprise one or more access openings 12 to permit access to the spacer 4 through the bone plate 2. Although the access opening 12 depicted in FIGS. 1A and 1B has a closed perimeter, in other embodiments of the invention, the access opening may have an open perimeter. One of skill in the art will understand that any of a variety of bone plates known in the art may be used or modified for use with the invention.

The interbody fusion implant 4 may comprise for one or more coupling sites 14, 16 on the trailing surface 18 of the implant 4 that are accessible through the access opening 12 of the plate 2. One of skill in the art will understand that any of a variety of spacer devices known in the art may be used or modified for use with the invention. For example, although the spacer 4 depicted in FIG. 1A is not configured for fixation to the adjacent vertebral bodies, in other embodiments of the invention the interbody fusion implants may include fastener apertures for fixation by bone screws or other fasteners. Other examples of interbody fusion implants that may be used with the invention include but are not limited to those disclosed in U.S. Design Pat. Nos. D533,277, D524,443, D539,934, and D541,940, the disclosures of which are herein incorporated by reference in their entirety.

Although the plate 2 and the spacer 4 are separate components, each component may also comprise one or more features or structures that are complementary to the other component. For example, the leading surface 8 of the plate 2 may have a recess or protrusion that provides a complementary fit to the trailing surface 18 on the spacer 4. An interfit between two or more implantable components, or between the coupler device and one or more components, may improve stability or alignment of the various components during the implantation procedure.

Figure 2A:
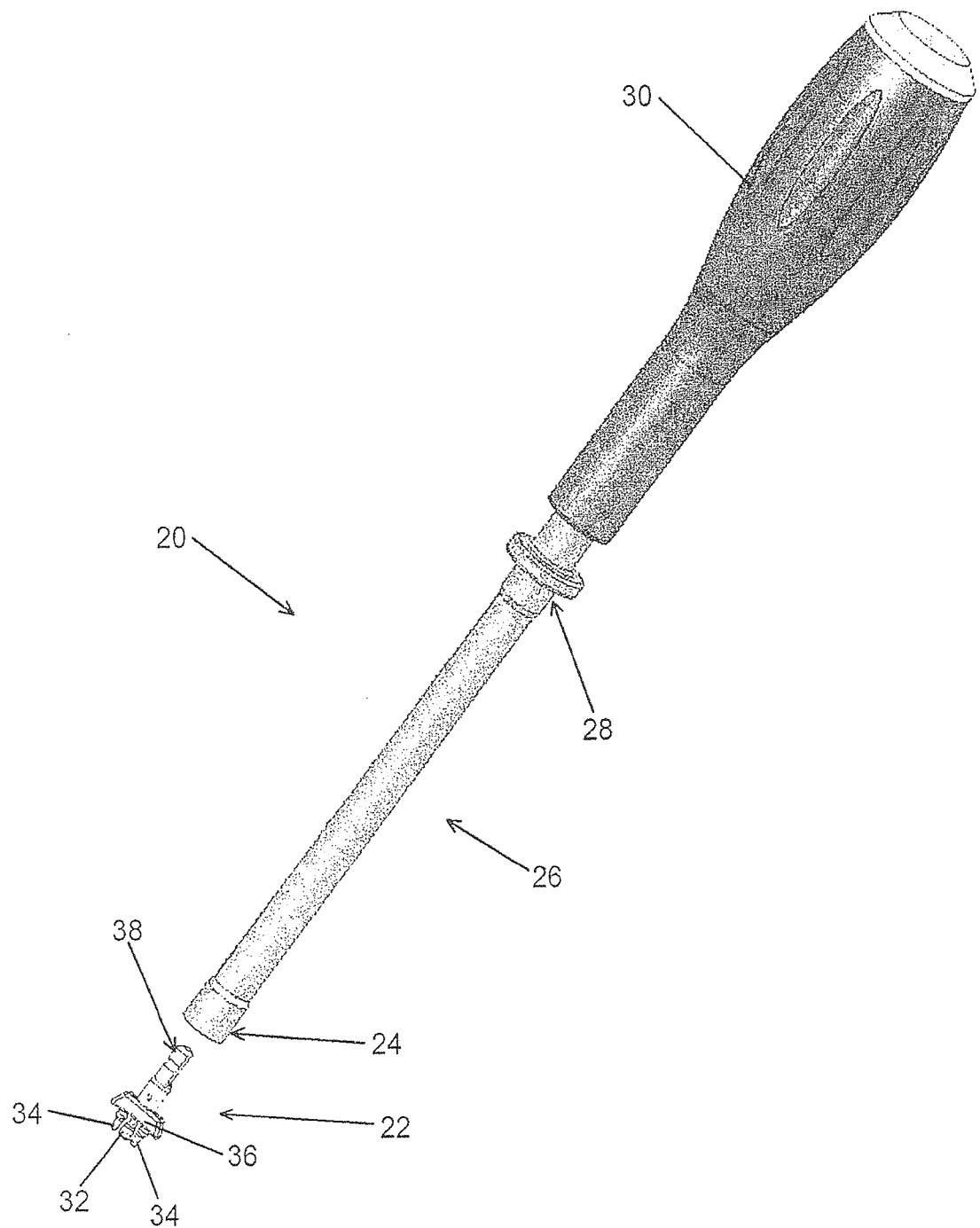
FIGS. 2A and 2B are perspective views of one embodiment of an implant coupler for performing dual-implantation.
Figure 2B:
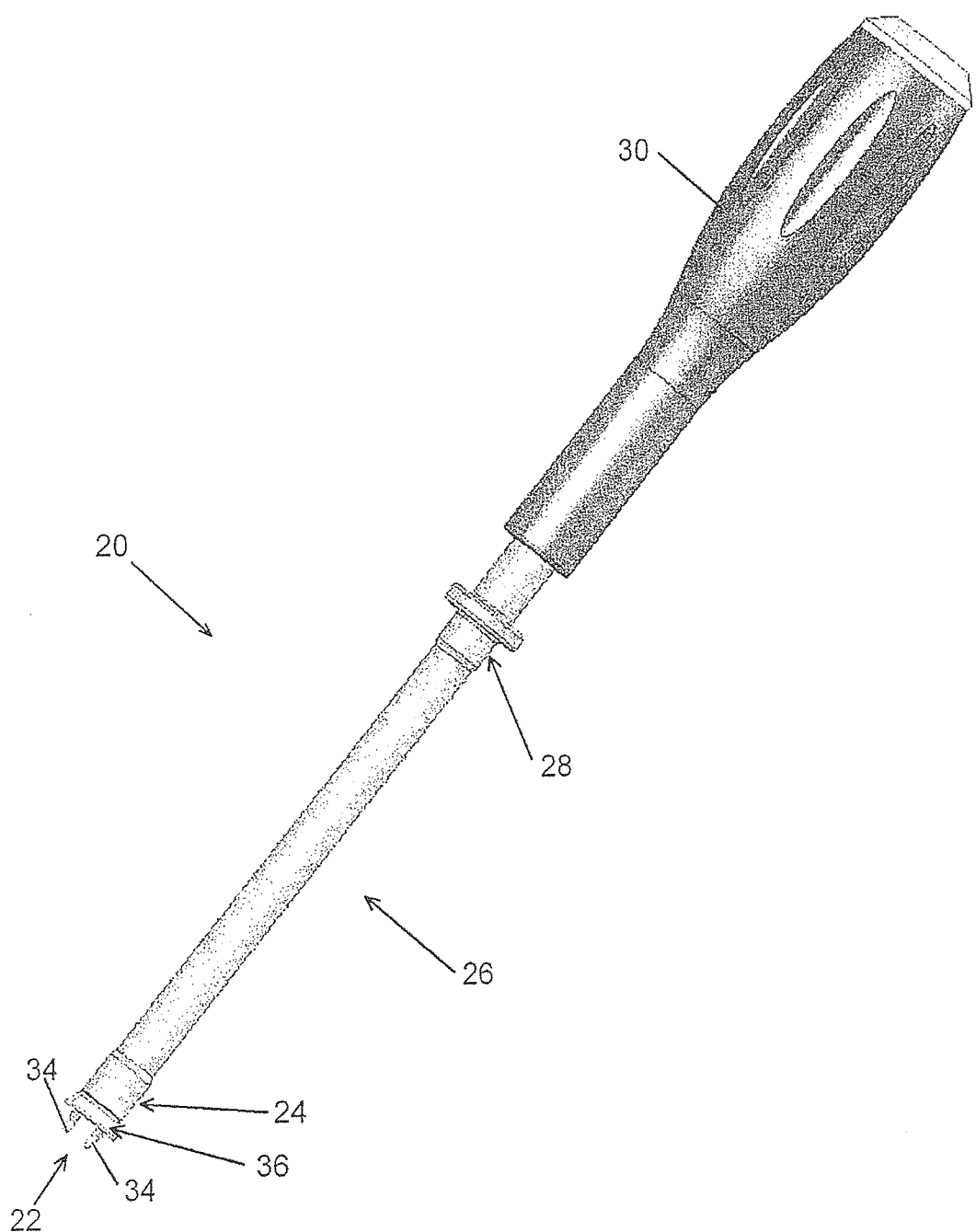

FIGS. 2A and 2B are perspective views of one embodiment of a delivery tool 20. As shown in FIG. 2A, the delivery tool 20 comprises a device coupler 22 that is detachably engageable to the distal end 24 of a shaft 26 of the delivery tool 20. FIG. 2B depicts the coupler 22 attached to the distal end 24 of the shaft. The proximal end 28 of the shaft 26 has a handle 30 that facilitates gripping of the delivery tool 20 and may also be configured to engage and manipulate the device coupler 22. In other embodiments, the delivery tool may comprise two or more shafts for providing multiple coupling sites on the delivery tool, or for coupling multiple implants in a side-by-side manner.

As can be seen in FIG. 2A, the device coupler 22 may comprise one or more coupling members 32, 34 extending from a coupling base 36. Proximally, the device coupler 22 may have a proximal attaching member 38 that is configured to disengageably attach to the distal end 24 of the shaft 26. The detachability of the device coupler 22 from the rest of the delivery tool 20 facilitates visibility of and access to the implantable components 2, 4 after the initial insertion of the delivery tool 20. In some embodiments of the invention, the attaching member 38 and one or more coupling members 32 are integrally formed and permits manipulation of the coupler member 32 using the handle 30 acting through the attaching member 38. In other embodiments, however, the coupler member 32 may be manipulated separately from the structures configured to provide attachment between the coupler 22 and the shaft 26.

FIGS. 3A through 3B depict the device coupler 22 detached from the delivery tool 20 and depicted in a relative relationship with the plate 2 and spacer 4 components of FIGS. 1A and 1B. This particular embodiment of the coupler 22 is configured to engage a distally located interbody fusion implant 4 while trapping or clamping the proximally located plate 2 between the fusion implant 4 and the coupler base 36. Thus, in this particular embodiment, the coupler 22 does not directly couple to the plate 2. Depending on the spacing(s) of the coupling members 32, 34 and the coupling sites 14, 16 relative to the size and shape of the access opening 12 shape, the fixation plate 2 may be generally moveable about a plane or zone between the prong base 36 and the spacer 4, depending upon the degree of clamping or trapping being provided. Thus, the plate 2 may be repositionable relative to the spacer 4 or delivery tool 20 while reducing the risk that the plate 2 may separate from the delivery tool 20. The lengths of one or more coupling members may also affect the amount of space between the distally attached component 4 and the coupling base 36, and therefore affect the amount of displacement out of the plane between the two components.

In the specific embodiment depicted in FIGS. 3A through 3C, the coupling device 22 comprises two fixed coupling members 34 located about a movable coupling member 32. These coupling members 32, 34 are configured to engage the complementary coupling sites 14, 16 on the spacer 4. As can be appreciated by one skilled in the art, the number and configurations of the coupling members 32, 34 provided on the delivery tool 20 can vary according to the particular orthopedic device. For example, in some embodiments, all of the coupling members may have a movable configuration, while in other embodiments; all of the coupling members may have a fixed configuration.

In the embodiment depicted in FIGS. 3A through 3C, the fixed coupling members 34 insert into coupling sites 16 to resist rotational movement between the spacer 4 and the delivery tool 20. Although the coupling members 34 are located at equal distances on opposite sides from the movable coupling member 32, the coupling members 32, 34 need not be configured to be equal in size in shape or to be symmetric with respect to a central plane or central axis of any of the implantable components or the delivery tool. In other embodiments, one or more coupling members or may have a cross-sectional shape that cannot be rotated in a complementary shaped recess on the implant, e.g. a square or oval shape. In further embodiments, the aligning or engaging prongs may be substituted for any of a variety of complementary mechanical interfaces. The coupling prongs 32, 34 may be configured with a corresponding shape, depth, spacing, and size to fit with the complementary coupling sites 14, 16 of the implant 4. For example, instead of fixed or movable coupling members 32, 34 configured to maintain least some alignment or position range between the delivery tool 20 and the implantable components 2, 4, an alignment structure or recess may be provided on the coupling base 36 that aligns with the edges or other structures on the implant to maintain the alignment between the implant and the delivery tool. In some embodiments, the coupling members may comprise opposing movable or pivotable grasping members configured to mechanically engage a variety of devices that need not be specifically designed for attachment to the delivery tool.

Although the coupling members 32, 34 depicted in FIGS. 3A to 3C are elongate members configured to insert into lumen-type coupling sites 14, 16 of the spacer 4, in other embodiments the elongate members may be located on the implant and the coupling lumens may be located on the delivery tool, and in still other embodiments, a different type of mechanical interfit may be used.

The bone plate 2 and interbody fusion implant 4 may be prepared for implantation by orienting the access opening 12 of the bone plate 2 against the anterior surface 18 of the implant 4, without obstructing the coupling sites 14, 16. To engage the delivery tool 20 to the implantable components, the movable coupling member 32 is extended to contact and engage the complementary coupling site 14 on the spacer 4.

Preferably, at least one coupling member 32, 34 of the delivery tool 20 comprises a locking configuration or structure to detachably engage one or more of the implantable orthopedic devices 2, 4. The locking or coupling mechanism may be provided on a movable coupling member 32 and may comprise, for example, any of a variety of complementary mechanical interfits with the coupled implant, such as a threaded lock, snap-on fitting, or an interlocking fit. In other embodiments, the interfit may be a friction fit or a magnetic fit. In one example, the coupling member or prong 32 comprises a threaded surface that engages a corresponding threaded lumen on the target orthopedic device 4. In some embodiments, in order to bring the corresponding threaded surfaces together, the coupling member 32 may be axially movable from a retracted position to an extended position. As can be seen in FIGS. 3B and 3C, the movable coupling member 32 is movable with respect to a lumen 40 of the coupling base 36, which in turn permits the attachment and detachment of the distal implant. The coupling member 32 may be movable longitudinally and rotationally until contact is made with the complementary coupling site 14, and then the coupling member 32 is rotatably threaded into the coupling site 14 on the anterior surface 18 of an implant 4. The coupling member 32 may be freely positionable from its disengaged position to its engaged position, or the coupling member 32 may be biased by a spring or other bias member in either position and to provide tactile feedback to the user as to the current state between the delivery tool and the implant(s).

In other embodiments, instead of a threaded coupling member 32, the coupling member may have a configuration that forms a mechanical interfit with the coupling site 14 of the distal implant. In still other embodiments, the coupling member 32 may comprise a movable hook that engages a recess or pin on the implantable device, or a pivot or clamp member that retain the components by grasping onto the sides of the components. As mentioned above, in some embodiments, the locking or coupling mechanism may be configured to generically couple devices of a general size or shape and need not be specifically configured to the delivery tool. One of skill in the art will understand that any of a variety of disengageable mechanisms known in the art may be used to detachably couple one or more implantable devices.

In other embodiments, two or more implantable components may be independently coupled to the delivery tool. For example, the delivery tool may be configured with two or more movable coupling members, with at least one movable coupling member detachably coupled to the plate 2 and at least one movable coupling member detachably coupled to the spacer 4. Independent attachment of each implantable component permits removal of the delivery tool 20 from the surgical site prior to completing attachment of all the implants without the risk that one or more proximal implants may fall off the delivery tool and be lost in the surgical site. In embodiments with multiple coupling members with locking mechanisms, two or more movable coupling members may be simultaneously manipulated by the same handle or control member, or may be controlled independently or separately.

In further embodiments, one or more coupling members 32, 34 may be detachably coupled to the coupling base 36 such that the coupling members may be removed, replaced, or substituted, depending upon the particular configurations of the devices being implanted.

As shown in FIG. 3C, the movable coupling member 32 and the fixed coupling members 34 may be configured to extend through the access opening 12 of a first orthopedic device 2 and to couple with the coupling sites 14, 16 of a second orthopedic device 4. In certain embodiments, the coupling base 36 is with a shape or size along at least one dimension transverse to access opening 12 of the plate 2 such that, in use, the base 36 does not pass through the access opening 12. In some embodiments, this transverse dimension of the coupling base 36 is greater than the largest transverse dimension of the access opening 12, while in other embodiments, the at least one transverse dimension of the coupling base 36 is merely larger than the smallest transverse dimension of the access opening 12. The distal surface 42 of the prong base 36 may be complementarily configured to lie against the trailing surface 6 of the fixation plate 2 to improve the stability and securement of the plate 2 when clamped between the base 36 and the distal implant 4.

As shown in the embodiment of FIGS. 3A to 3C, the device coupler 22 may further comprise a proximal attaching structure 38 for detachably engaging the device coupler 22 to the shaft 26 of the delivery tool 20. The proximal attaching structure 38 comprises a proximal end 44, a distal end 46 that is joined to the movable coupling member 32. In some embodiments, the proximal attaching structure 38 and the movable coupling member 32 are integrally formed. To facilitate detachable engagement, the proximal attaching structure 38 may be configured with one or more features that permit user-controlled locking and unlocking of the device coupler 22 from the shaft 26 of the delivery tool 20, such as a recess 48 on the proximal attaching structure 38. The function of the recess 48 is explained in greater detail below.

Figure 4:
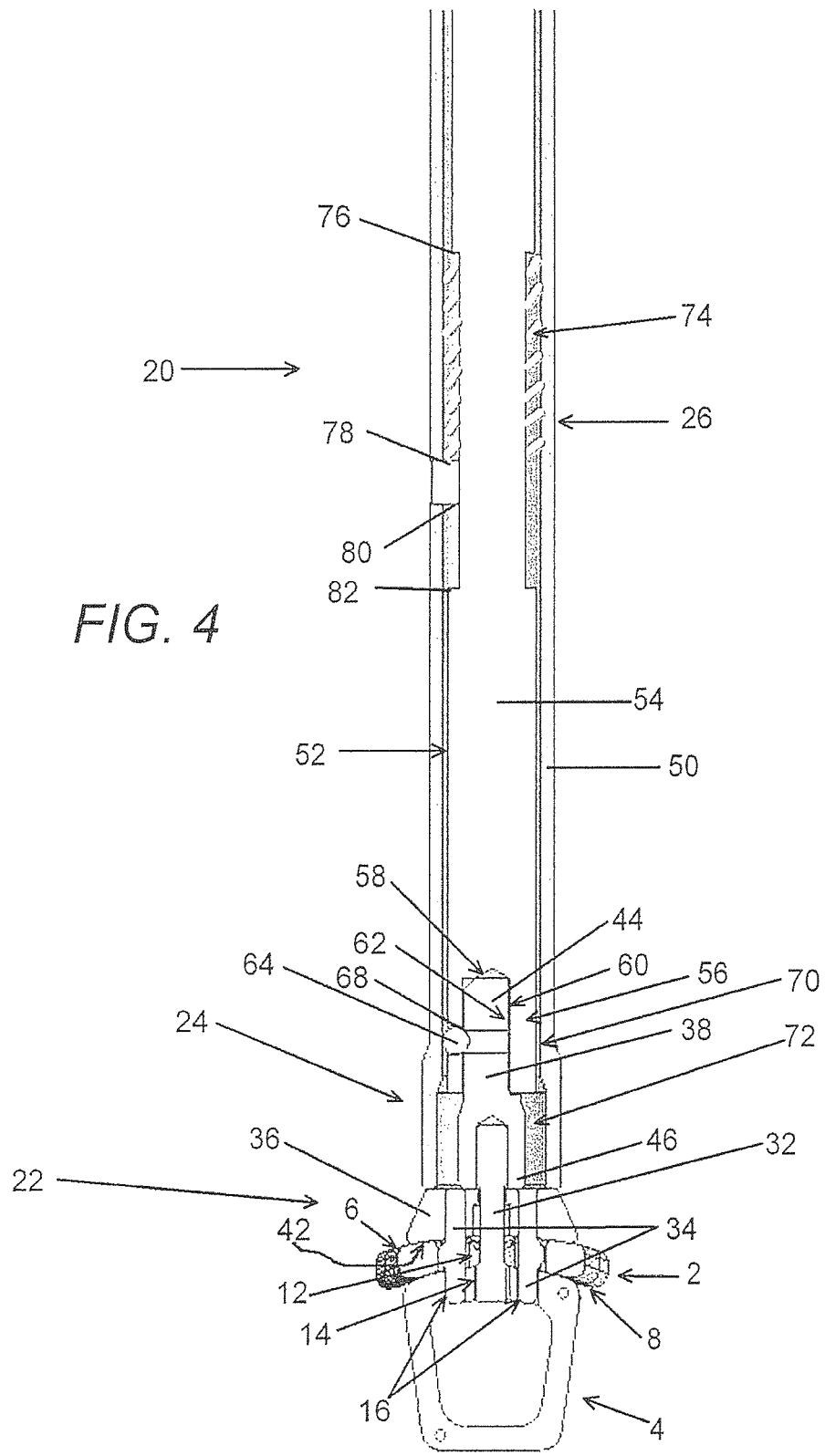
FIG. 4 is a cross-sectional view of a device coupler coupling together the bone plate and the interbody fusion implant.

FIG. 4 depicts a cross-sectional view of the embodiment of the delivery tool 20 and device coupler 22 coupled to a bone plate 2 and an interbody fusion implant 4. The shaft 26 comprises an outer tubular shaft 50 with a lumen 52 and an inner shaft 54 residing within the lumen 52. The inner shaft 54 is attached proximally to the handle 30 while the distal end 56 of the inner shaft 54 is configured to engage the attaching member 38 of the device coupler 22. The inner shaft 54 and the lumen 52 of the outer tubular shaft 50 are preferably configured to permit a relative motion between the two structures 50, 54.

The attaching member 38 is preferably configured to form a detachable mechanical interfit with an inner lumen 58 of the inner shaft 54. To permit the transfer of rotational force from the handle 30 to the attaching member 38 inserted into the inner lumen 58, the proximal end 44 of the attaching member 38 and the inner lumen 58 preferably have complementary non-circular cross-sectional shapes. For example, referring back to FIGS. 3A to 3C, the proximal end 44 of the attaching member 38 comprises a non-circular structure or surface 60 through which a complementary non-circular structure or surface 62 in the inner lumen 58 can transfer rotational force.

To reduce detachment of the device coupler 22 from the inner shaft 54 during the implantation procedure, a locking assembly may be provided. As shown in the embodiment of FIG. 4, a locking element 64, such as a ball bearing, may be used to provide an interference fit between the shaft 26 of the delivery tool 20 and the device coupler 22. The locking element 64 may reside within a lumenal wall aperture 68 of the inner shaft 54 and comprises a locking position where the locking element 64 protrudes from the lumenal wall aperture 68 into the inner lumen 58 and into the recess 48 on attaching member 38. The locking element 64 may be maintained in the locking position by a section of reduced diameter 70 of the lumen 52 of the outer tubular shaft 50. To avoid having the locking element 64 come out of the lumenal wall aperture 68 when the attaching member 38 is not inserted, the locking element 64 is preferably configured with a cross-sectional shape or size that is larger than the lumenal wall aperture 68. For example, if the locking element is a ball bearing, the lumenal wall aperture 68 preferably has a diameter that is smaller than the diameter of the ball bearing.

To permit the unlocking of the locking element 64 from the attaching member 38, the outer tubular shaft 50 further comprises a section of enlarged diameter 72 than the section of reduced diameter 70 which permits displacement of the locking element 64 into the section of greater diameter 72 and remove the interference fit with the recess 48. Preferably, the outer tubular shaft 50 is configured so that the user can manipulate the delivery tool 20 between the locked and unlocked positions. In the embodiment depicted in FIG. 4, the sections of reduced and enlarged diameters 70, 72 are longitudinally displaced along the longitudinal axis of the delivery tool 20 and the user can manipulate the delivery tool 20 between the two positions by pulling and pushing the outer shaft 50 relative to the inner shaft 54, which controls whether the locking element 64 is exposed to either the section of reduced or enlarged diameter 70, 72.

In some embodiments of the inventions, the delivery tool 20 may be optionally provided with a bias to the locked or unlocked position. For example, in the particular embodiment depicted in FIG. 4, a spring 74 or other bias member is provided between a proximal transverse surface 76 of the inner shaft 54 and a distal transverse surface 78 of the outer shaft 50, which provides a bias to the locked position. If a delivery tool with a bias to the unlocked position is desired, a spring or biased member may be provided between a proximal transverse surface 80 of the outer shaft 50 and a distal transverse surface 82 of the inner shaft 54. One of skill in the art will understand that in other embodiments, the locations of the proximal and distal surfaces or structures may be reversed, and that other bias structures may be used.

The recess 48 on the proximal end 44 of the attaching member 38 may have a convex surface to facilitate displacement of the locking element 64 out of the recess 48 when the delivery tool 20 is in the unlocked position. In other embodiments, however, a recess with perpendicular side walls may be preferred to reduce inadvertent slippage of the locking element out of the recess. In these embodiments, to reduce the risk of snagging or sticking between the locking element and the recess, a locking element having an outward bias, such as a C-ring, may be used. In other embodiments of the invention, the locking element and the recess may be configured so that the proximal attaching member 38 of the device coupler 22 can automatically snap-in and lock into the inner shaft 54 when inserted, without requiring that the user pull back on the outer shaft 50. For example, the proximal surface of an inwardly biased locking element and/or the proximal end of the attaching member may be provided with a ramped surface to facilitate insertion of the proximal end of the attaching member past the biased element and to snap into the recess of the attaching member. One of skill in the art will understand that any of a variety of locking mechanisms may be used between the shaft 26 and the device coupler 22, including but not limited to pin-type locks that may be slide or push-button actuated, magnetic locks, etc.

A variety of structures may also be provided on the delivery tool 20 to restrict movement between the outer shaft 50 and the inner shaft 54. Such structures may also be helpful to the users by providing visual or tactile feedback as to the locked or unlocked state of the delivery tool. In the embodiments shown in FIGS. 5A and 5B, for example, a stop structure 84 is provided at the proximal end 28 of the shaft 26 to restrict the proximal movement of the outer shaft 50 relative to the inner shaft 54 and handle 30. The distance between the handle 30 and the stop 84 also indicates to the user whether the delivery tool 20 is in the locked or unlocked state, or whether the locking mechanism has jammed or malfunctioned. In FIG. 5A, for example, a plate 2 and spacer 4 have been pre-attached to a device coupler 22, and is being inserted into the inner lumen 58 of the inner shaft 54 after the outer shaft 50 has been pulled back into the unlocked position. The unlocked position permits the locking element 64 depicted in FIG. 4 to displace outward into the section of enlarged diameter 72 and for the attaching member 38 of the device coupler 22 to fully insert into the inner lumen 58 of the inner shaft 54 and for the locking element 64 to form an interference fit with the recess 48 of the attaching member 38. Referring back to FIG. 5B, the outer shaft 50 is then moved back into its distal locked position, either manually by the surgeon or by releasing the outer shaft 50 and having a bias structure optionally contained in the shaft 26 to move and secure the delivery tool 20 in the locked position.

Each component of the delivery tool may comprise the same or different materials. Any of a variety of metals, plastics, ceramics, or other materials known in the art may be used. In some embodiments, radiolucent materials may be preferred, especially for the device coupler. Radiolucent materials allow the surgeon to initially insert the spacer implant and radiographically verify the desired result of the spacer before continuing the remaining portions of the procedure. In other embodiments, one or more radioopaque components may be provided.

In some embodiments of the invention, a kit or system for performing orthopedic fixation made is provided. The kit comprises a delivery tool comprising a handle and a shaft and a device coupler. The device coupler may be supplied either attached or separated from the shaft. In some kits or systems, multiple device couplers may be provided. This permits the surgeon or user to pre-attach a number of plates and spacers for insertion during the procedure without having to re-use the same device coupler. This may reduce the time required to perform the surgery or procedure. When multiple device couplers are provided in a kit, the device couplers may have the same or different size or configuration. In other embodiments, multiple shafts of different lengths are provided. In some embodiments of the kit or system, the plate and spacer may be coupled to the device coupler either during manufacturing or at the point-of-use. In some embodiments, the kit or system comprises only the device coupler with a pre-coupled fixation plate and pre-coupled spacer.

In one embodiment of the invention, a method for performing spinal fixation is provided. The patient is prepped and draped in the usual sterile fashion and anesthesia is achieved. The portion of vertebral column to be treated is accessed and the interbody space is prepared for insertion of the fusion implant. A delivery tool is inserted through a selected fixation plate and attached to the interbody fusion implant using a threaded coupling member. The coupling member is tightened until the fixation plate is clamped or secured between the interbody fusion implant and the delivery tool. Alternatively, a prepackaged device coupler with a pre-coupled fixation plate and spacer is attached to the shaft of a delivery tool. The fusion implant is inserted and seated into the interbody space using the delivery tool and the positioning of the implant is confirmed visually or radiographically. The fusion implant may be repositioned if necessary. The threaded coupling member is partially released to permit some movement of the fixation plate and the final position of the plate is determined. The fixation plate is then fixed to the surface of the two vertebrae adjoining the intervertebral space where the fusion implant was inserted. In some further embodiments, fixation of the plate may comprise pulling back on the outer shaft of the delivery tool and separating the device coupler from the proximal delivery tool. The handle and shaft may be reattached to the device coupler after one or more or all of the fixation plate fasteners have been inserted and the handle is rotated or manipulated to unscrew or detach the movable coupling member from the fusion implant. During or after fixation of the plate is completed, the alignment of the spine is checked visually or radiographically to reconfirm correct placement and/or effect from the implants. In some cases, the device coupler may be reattached to the fusion implant to reposition it. The surgical site is closed and dressed when the procedure is completed.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the disclosed invention. For all the embodiments described above, the steps of the methods need not be performed sequentially. Thus, it is intended that the scope of the present invention herein disclosed should not be limited by the particular disclosed embodiments described above, but should be determined only by a fair reading of the claims that follow.

What is claimed is:

1. A surgical delivery tool, comprising:
    an outer tubular shaft having a proximal end, a distal end and a lumen therebetween;
    an inner tubular shaft having a proximal end, a distal end, wherein the inner tubular shaft is located at least partially in the lumen of the outer tubular shaft;
    a handle located at the proximal end of the inner tubular shaft;
    a device coupler wherein the device coupler comprises a coupling base with a through lumen and an elongate coupling member comprising a proximal end and a distal end, wherein the distal end is configured with at least one radial projecting structure configured to abut the coupling base and the proximal end is configured to releasably engage the distal end of the inner tubular shaft, wherein at least a portion of the elongate coupling member is configured so as to move in the through lumen of the coupling base such that the elongate coupling member has a proximal position and a distal position, wherein, in the proximal position, the radial projecting structure on the distal end of the elongate coupling member abuts a distal surface of the coupling base and in the distal position the radial projecting structure lies distal to and separated from the distal surface of the coupling base; and
    a releasable lock assembly located about the distal end of the inner tubular shaft and configured to releasably engage the proximal end of the elongate coupling member of the device coupler.

2. The surgical delivery tool of claim 1, further comprising two distal coupling members fixed to the distal surface of the coupling base, wherein the distal coupling members are adapted to engage complementary structures on a proximal surface of an implant.

3. The surgical delivery tool of claim 1, wherein the distal end of the inner shaft comprises a distal lumen, a lumenal surface, an ablumenal surface, and a lock lumen between the lumenal surface and the ablumenal surface.

4. The surgical delivery tool of claim 3, wherein the distal lumen of the inner shaft comprises a non-circular cross-sectional shape.

5. The surgical delivery tool of claim 4, wherein the proximal end of the elongate coupling member has a configuration that forms a mechanical interfit with the distal lumen of the inner shaft.

6. The surgical delivery tool of claim 3, wherein the lock lumen has a luminal opening and an ablumenal opening.

7. The surgical delivery tool of claim 6, wherein the luminal opening has at least one dimension that is smaller than the ablumenal opening.

8. The surgical delivery tool of claim 6, wherein the releasable lock assembly is located at least partially within the lock lumen of the inner shaft.

9. The surgical delivery tool of claim 8, wherein the releasable lock assembly comprises a lock element having a lock position wherein the lock element protrudes through the lumenal opening and a release position wherein the lock element does not protrude through the lumenal opening.

10. The surgical delivery tool of claim 9, wherein the lumen of the outer tubular shaft has art enlarged cross-sectional area about the distal end of the outer tubular shaft.

11. The surgical delivery tool of claim 9, wherein the lock element is a ball bearing.

12. The surgical delivery tool of claim 1, further comprising a bias member within the lumen of the outer shaft.

13. The surgical delivery tool of claim 12, wherein the bias member is configured to bias the lock element in the lock position.

14. The surgical delivery tool of claim 1, wherein the coupling base comprises a distal concave surface.

15. The surgical delivery tool of claim 1, wherein the inner shaft and the outer tubular shaft are configured to permit at feast some relative rotational movement between the inner shaft and the outer tubular shaft.

16. The surgical delivery tool of claim 1, wherein the inner shaft and the outer tubular shaft are configured to permit at least some relative axial movement between the inner shaft and the outer tubular shaft.

17. The surgical delivery tool of claim 1, wherein the elongate coupling member is integrally formed.

18. A system for performing an orthopedic procedure, comprising:
    a first orthopedic implant configured with a first access opening;
    a second orthopedic implant having a second access opening and at least one transverse dimension that is larger than the smallest transverse dimension of the first access opening; wherein the second orthopedic implant has a different configuration from the first orthopedic implant; and
    a delivery tool comprising a retaining surface and one or more coupling sites wherein at least one coupling a distal elongate coupling member;
    wherein the retaining surface comprises at least one transverse dimension that is larger than the smallest transverse dimension of the first access opening;
    wherein the at least one distal elongate coupling member is configured to simultaneously pass through the first access opening of the first orthopedic implant and to form a mechanical interfit with the second access opening of the second orthopedic implant so as to retain the first orthopedic implant by compression between the retaining surface and the second orthopedic implant and without forming a mechanical interfit between the retaining surface of the delivery tool and the first orthopedic implant; and
    wherein the retaining surface and the distal elongate coupling member are configured to releasably detach from the delivery tool.

19. The system for performing an orthopedic procedure as in claim 18, wherein the first orthopedic implant is a fixation plate.

20. The system for performing an orthopedic procedure as in claim 18, wherein the second orthopedic implant is an interbody vertebral spacer.

21. The system for performing an orthopedic procedure as in claim 20, wherein the interbody vertebral spacer is an interbody cervical spacer.

22. The system for performing an orthopedic procedure as in claim 18, wherein the mechanical interfit between the delivery tool and the second access opening of the second orthopedic implant comprises a mechanical interfit.

23. The system for performing an orthopedic procedure as in claim 18 wherein the first access opening of the first orthopedic implant is larger in at least one transverse dimension than the corresponding transverse dimension of the area occupied by the one or more coupling sites and wherein the first orthopedic implant is not coupled to the second orthopedic implant during insertion such that the first orthopedic implant may be repositionable relative to the second orthopedic implant and the delivery tool while the delivery tool is coupled to the second orthopedic implant.

24. A system for performing an orthopedic procedure, comprising:
- a first orthopedic implant configured with a first access opening;
- a second orthopedic implant having a second access opening and at least one transverse dimension that is larger than the smallest transverse dimension of the first access opening; wherein the second orthopedic implant has a different configuration from the first orthopedic implant; and
- a delivery tool comprising
  - a device coupler comprising a coupling base with a through lumen, a proximal surface, and a distal retaining surface
  - and an elongate coupling member comprising a proximal end and a distal end, wherein the distal end of the coupling member is configured with at least one radial projecting structure configured to abut the distal retaining surface of the coupling base,
  - wherein at least a portion of the elongate coupling member is configured so as to move in the through lumen of the coupling base such that the elongate coupling member has a retracted position and an extended position,
  - wherein, when the elongate coupling member is in the retracted position, the radial projecting structure on the distal end of the elongate coupling member abuts the distal retaining surface of the coupling base and is not coupled to the second orthopedic implant and in the extended position of the elongate coupling member, the radial projecting structure lies distal to and separated from the distal retaining surface of the coupling base and is detachably coupled to the second orthopedic implant.

* * * * *

UNITED STATES PATENT AND TRADEMARK OFFICE
CERTIFICATE OF CORRECTION

Page 1 of 1

PATENT NO.        : 8,500,811 B2
APPLICATION NO.   : 12/167173
DATED             : August 6, 2013
INVENTOR(S)       : Blain et al.

It is certified that error appears in the above-identified patent and that said Letters Patent is hereby corrected as shown below:

In the Claims:

In column 12 at line 5, In Claim 10, change "art" to --an--.

In column 12 at line 18, In Claim 15, change "feast" to --least--.

In column 12 at line 37, In Claim 18, change "coupling a" to --coupling site is a--.

Signed and Sealed this
Twenty-ninth Day of April, 2014

Michelle K. Lee
*Deputy Director of the United States Patent and Trademark Office*